US006706747B2

(12) United States Patent
Munk et al.

(10) Patent No.: US 6,706,747 B2
(45) Date of Patent: *Mar. 16, 2004

(54) CONFORMATIONALLY RIGID BICYCLIC AND ADAMANTANE DERIVATIVES USEFUL AS $\alpha_2$-ADRENERGIC BLOCKING AGENTS

(75) Inventors: Stephen A. Munk, Northville, MI (US); James A. Burke, Santa Ana, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/393,313

(22) Filed: Mar. 19, 2003

(65) Prior Publication Data

US 2003/0187047 A1 Oct. 2, 2003

Related U.S. Application Data

(63) Continuation of application No. 09/846,399, filed on May 1, 2001, now Pat. No. 6,569,884, which is a continuation of application No. 09/542,216, filed on Apr. 4, 2000, now Pat. No. 6,319,935, which is a continuation of application No. 09/003,902, filed on Jan. 7, 1998, now Pat. No. 6,150,389, which is a continuation-in-part of application No. 08/538,694, filed on Oct. 3, 1995, now Pat. No. 5,731,337, which is a continuation of application No. 08/273,521, filed on Jul. 11, 1994, now abandoned.

(51) Int. Cl.[7] ..................... A61K 31/421; C07P 263/08; A61P 3/04; A61P 3/10; A61P 15/10
(52) U.S. Cl. ..................... 514/370; 514/377; 548/190; 548/193; 548/234
(58) Field of Search ............... 514/370, 377; 548/190, 193, 234

(56) References Cited

U.S. PATENT DOCUMENTS

| | | | |
|---|---|---|---|
| 2,870,159 A | 1/1959 | Bloom | 260/307 |
| 2,876,232 A | 3/1959 | Bloom | 260/307 |
| 3,108,998 A | 10/1963 | Poos | 260/247.2 |
| 3,133,901 A | 5/1964 | Poos | 260/558 |
| 3,278,382 A | 10/1966 | Poos | 167/65 |
| 3,432,600 A | 3/1969 | Harvey, Jr. | 424/272 |
| 3,453,284 A | 7/1969 | Harvey, Jr. | 260/307 |
| 3,509,170 A | 4/1970 | Levitt | 260/307 |
| 3,514,486 A | 5/1970 | Hartzler | 260/563 |
| 3,598,833 A | 8/1971 | Hiltmann et al. | 260/307 |
| 3,624,092 A | 11/1971 | Levitt | 260/288 R |
| 3,636,219 A | 1/1972 | Culik et al. | 424/265 |
| 3,679,798 A | 7/1972 | Culik et al. | 424/265 |
| 4,064,348 A | 12/1977 | Peet et al. | 544/137 |
| 4,256,755 A | 3/1981 | Smith, Jr. | 424/272 |
| 4,515,800 A | 5/1985 | Cavero et al. | 514/392 |
| 4,587,257 A | 5/1986 | DeSantis et al. | 514/392 |
| 4,590,202 A | 5/1986 | Remy | 514/392 |
| 4,980,364 A | 12/1990 | Goodman | 514/377 |
| 5,066,664 A | 11/1991 | Gluchowski | 514/377 |
| 5,091,528 A | 2/1992 | Gluchowski | 544/105 |
| 5,580,892 A | 12/1996 | Garst et al. | 514/377 |
| 5,731,337 A | 3/1998 | Munk et al. | 514/377 |
| 5,837,751 A | 11/1998 | Jacobine et al. | 522/167 |
| 6,319,935 B1 * | 11/2001 | Munk et al. | 514/370 |

FOREIGN PATENT DOCUMENTS

| EP | 0251453 | 1/1988 |
|---|---|---|
| GB | 1021012 | 2/1966 |

OTHER PUBLICATIONS

Banert et al, Journal of the American Chemical Society, 1982, 104, pp. 3766–3767, "Sn2 Displacements at 2–Norbornyl Brosylates".
Registry No. 101832–33–1 (1986).
Poos, et al, Journal of Organic Chemistry, 1961, 26, 4898–4904, "Bicyclic Bases III. Isomeric 2–Amino–3–phenylnorboranes[1]".

* cited by examiner

Primary Examiner—Brenda Coleman
(74) Attorney, Agent, or Firm—Robert J. Baran; Martin A. Voet; Carlos A. Fisher

(57) ABSTRACT

A compound of formula I

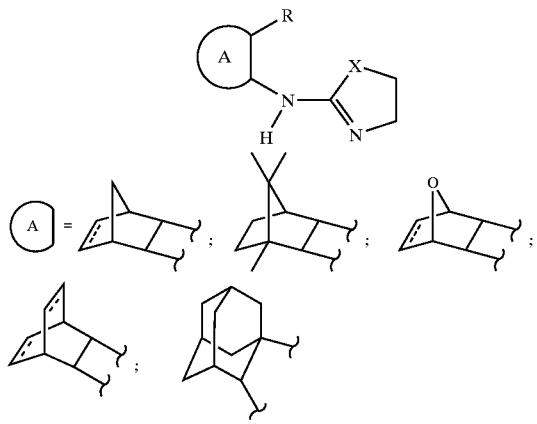

in which: ring A is one of the five alternative multi-cyclic rings as shown wherein a dotted line adjacent to a bond indicates that a single bond or a double bond may be present at that position; X is nitrogen, oxygen or sulfur; R is hydrogen, lower straight or branched chain alkyl of 1 to 6 carbon atoms, or lower straight or branched chain alkenyl of 2 to 6 carbon atoms, a cycloaliphatic ring of 3 to 6 carbon atoms, phenyl optionally mono- or di-substituted with hydroxy, halogen, alkyl of 1 to 3 carbon atoms or alkoxy of 1 to 2 carbon atoms, or methylenedioxyphenyl; or a stereoisomer, or a pharmaceutically acceptable salt thereof.

These compounds have $\alpha_2$ receptor blocking activity and hence find use in the treatment or palliation of elevated intraocular pressure, non insulin-dependent diabetes, male impotence and obesity.

10 Claims, No Drawings

US 6,706,747 B2

CONFORMATIONALLY RIGID BICYCLIC AND ADAMANTANE DERIVATIVES USEFUL AS α₂-ADRENERGIC BLOCKING AGENTS

CROSS REFERENCE TO RELATED APPLICATIONS

This patent application is a continuation of Ser. No. 09/846,399; filed May 1, 2001 now U.S. Pat. No. 6,569,884; which is a continuation of Ser. No. 09/542,216 filed Apr. 4, 2000; now U.S. Pat. No. 6,319,935; which is a continuation of Ser. No. 09/003,902 filed Jan. 7, 1998, now U.S. Pat. No. 6,150,389; which is a continuation in part of Ser. No. 08/538,694 filed Oct. 3, 1995; now U.S. Pat. No. 5,731,337; which is a file wrapper continuation of 08/273,521 filed Jul. 11, 1994, now abandoned.

FIELD OF THE INVENTION

The present invention relates to aliphatic bridged-cyclic compounds with 2-amino-imidazoline, 2-amino-oxazoline or 2-amino-thiazoline substituents. More particularly, the invention relates to such compounds which are selective in blocking the $\alpha_2$ adrenoreceptor. These compounds find use in the treatment of conditions which are responsive to regulation of $\alpha_2$-receptor responses, such activities include, for example, treatment of depression, palliation of non insulin-dependent diabetes, alleviation of male impotence, lowering of intraocular pressure (which is useful in treating e.g. glaucoma) and stimulation of weight loss.

BACKGROUND OF THE INVENTION

Adrenergic agents, and particularly agents affective on $\alpha_2$ adrenergic receptors are known in the art. For example, U.S. Pat. No. 5,091,528 describes 6- or 7-(2-imino-2-imidazoline)-1,2-benzoxazine as a adrenergic agent. Published European patent application 0 251 453 describes certain cyclohexyl substituted amino-dihydro-oxazoles, -thiazoles and -imidazoles as $\alpha_2$ agents. U.S. Pat. No. 3,598,833 describes 2-cycloalkylamino oxazolines having local anesthetic, sedative, vasoconstrictor, mucous membrane de-swelling, blood pressure depressant and gastric fluid secretory inhibition effects. Further United States and foreign patents and scientific publications which pertain to substituted amino-oxazoline, imidazolines and thiazolines are as follows:

U.S. Pat. No. 4,587,257 [2-trisubstituted phenylimino) imidazoline compounds capable of controlling ocular bleeding];

U.S. Pat. No. 3,636,219 [2-(substituted-phenylamino)-thiazolines and imidazolines having anticholinergic activity];

U.S. Pat. No. 3,453,284 [2-substituted anilino)-2-oxazolines;

U.S. Pat. No. 3,432,600 [partially reduced 2-(naphthylamino) oxazolines and 2-(indanylamino) oxazolines;

U.S. Pat. No. 3,679,798 [compositions comprising arylaminooxazolines and an anticholinergic agent];

U.S. Pat. No. 3,624,092 [amino-oxazolines useful as central nervous system depressants];

U.S. Pat. No. 2,876,232 [2-(9-fluorenylamino)-oxazolines), and German Patent nos. 1,191,381 and 1,195,323 and European Patent Application no 87304019.0;

U.S. Pat. No. 4,515,800 [2-(trisubstituted phenylimino) imidazoline compounds, also known as 2-(trisubstituted-anilino)-1,3-diazacyclopentene-(2) compounds, for treatment of glaucoma];

U.S. Pat. No. 5,066,664 [2-(hydroxy-2-alkylphenylamino)-oxazolines and thiazolines as anti-glaucoma and vasoconstrictive agents].

Chapleo et al. journal of Medicinal Chemistry 1989, 32, 1627–30] describe heteroaromatic analogs of clonidine as partial agonists of $\alpha_2$ adrenoceptors.

Poos, et al. [Journal of Organic Chemistry, 1961, 26, 4898–904.] reported the syntheses of isomeric forms of 2-amino-3-phenylnorbornanes, and that the endo-phenyl-exo-amino compounds demonstrated a biphasic effect on blood pressure. U.S. Pat. No. 3,514,486 to Hartzler discloses making 3-isopropyl-2-norbornanamine and reports that they have useful antihypertensive activity.

Additionally, commonly assigned co-pending application Ser. Nos. 08/186,406 and 08/185,653 disclose alpha-substituted derivatives of aromatic 2-amino-imidazoles and methods of using the same as $\alpha_{2A}$ selective agonists.

The background of the division of adrenoceptors into differing categories can be briefly described as follows. Historically, adrenoceptors were first divided into α and β subtypes by Ahlquist in 1948. This division was based on pharmacological characteristics. Later, β-adrenoceptors were subdivided into $\beta_1$ and $\beta_2$ subtypes, again based on a pharmacological definition by comparison of the relative potencies of 12 agonists. The α-adrenoceptors were also subdivided into $\alpha_1$ and $\alpha_2$ subtypes, initially based on a presumed localization of $\alpha_1$ receptors postsynaptically and $\alpha_2$ presynaptically. Now, however, this physiologic division is no longer used and it is generally accepted that the most useful way to subdivide the a-adrenoceptors is based on pharmacology, using affinities for the a-antagonists yohimbine and prazosin. At $\alpha_1$ receptors, prazosin is more potent than yohimbine, whereas at $\alpha_2$ receptors, yohimbine is more potent than prazosin. More recently the $\alpha_1$ and $\alpha_2$ receptors have been further subdivided into subtypes such as $\alpha_{1A}$, $\alpha_{1B}$, $\alpha_{1C}$, $\alpha_{2A}$, $\alpha_{2B}$ and $\alpha_{2C}$.

The term agonist refers to a class of compounds which bind with some affinity to and activate a particular type of receptor. Activation refers to what could be considered analogous to flipping on a switch, i.e. the receptor is induced to initiate some kind of action like a physiologic response or a chain of biochemical events. The term antagonist (or receptor blocker) refers to a class of compounds which bind to a receptor with some affinity, but are unable to activate the receptor to provide an effect. The antagonist can be compared to a key which is able to slide into a lock, but is unable to turn in the lock to open it.

Some examples of alpha₂ ($\alpha_2$) adrenergic receptor blocking compounds known in the art are:

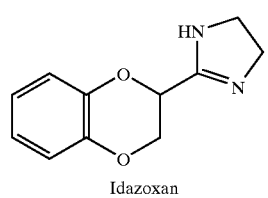

Idazoxan

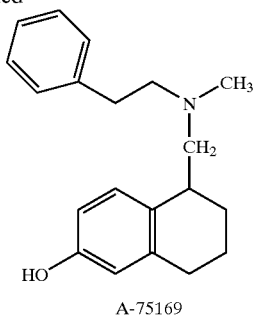

A-75169

Idazoxan is classified as a selective α₂ antagonist, and has been studied in combination with, tyrosine as an antidepressant and in combination with D₂ dopamine receptor antagonists as an antipsychotic agent. 1,2,3,4-tetrahydro-6-hydroxy-1-((N-methyl-amino)-methyl-N-phenylethyl) naphthalene hydrochloride (A-75169) lowers intraocular pressure in mammals.

The receptor affinity of candidate compounds can be determined by radioligand binding competition studies. Radioligand binding competition studies assess the affinity of a compound by measuring its ability to displace a radioligand of known affinity.

As described above, an agonist is defined as a compound that binds to and activates a receptor response. An antagonist binds to, but does not activate; a response by, the receptor. The measure of activation caused by a bound molecule is said to be its efficacy. Functional experiments are designed to determine whether, after binding, a test compound elicits a biochemical effect, or rather binds without causing the receptor to respond. An antagonist, if of sufficient binding affinity, can be used to block the binding of endogenous molecules in the body which activate a receptor, and thereby prevent its activation. Antagonists can find therapeutic use by blocking the binding of an oversupply of an endogenous receptor activator or the over expression of a receptor effect. Owing to the intricacy of the interactions between a given binding molecule and the conformation and function of the receptor itself, partial agonists and partial antagonists are also known in receptor pharmacology.

SUMMARY OF THE INVENTION

The present invention concerns novel compounds of the formula I, in which: ring A is any of the five alternative multi-cyclic rings shown, X is nitrogen, oxygen or sulfur and R is hydrogen, straight or branched chain alkyl of 1 to 6 carbon atoms, or straight or branched chain alkenyl of 2 to 6 carbon atoms, a cycloaliphatic ring of 3 to 6 carbon atoms, phenyl optionally mono- or di-substituted with hydroxy, halogen, alkyl of 1 to 3 carbon atoms or alkoxy of 1 to 2 carbon atoms, or methylenedioxyphenyl. In the drawing of chemical structures as shown above, the intersection of two or more lines indicates a carbon atom, a single line indicates a single bond, and a double line a double bond, and a dotted line adjacent a single line indicates either a single or double bond. The chemical nomenclature for the rings shown above from left to right in descending order is norbornane (or bicyclo[2.2.1]heptane); bornane (or 1,7,7-trimethyl-bicyclo [2.2.1]heptane; 7-oxa-bicyclo[2.2.1]heptane; bicyclo[2.2.2] octane and adamantane (or tricyclo[3.3.1.13,7]decane). The wavy lines across a bond indicate that the bond attaches to either the R or 2-amino-heterocyclic moieties. Any stereoisomers and diastereomers which are available by bonding the substituents R and the 2-amino-heteroazole moieties to the available valences of the above-indicated carbons on the rings are contemplated by the invention, as well as the pharmaceutically acceptable salts.

Another aspect of the invention concerns the method of use of these compounds in blocking or antagonizing α₂ receptor function.

Other aspects of the invention relate to pharmaceutical compositions containing the compounds of the invention in admixture with one or more pharmaceutically acceptable, non-toxic carriers, and to methods pertaining to their use.

DETAILED DESCRIPTION OF THE INVENTION

DEFINITIONS

As Used Herein

The terms "ester" and "amide" refer to and cover any compound falling within the definition of those terms as classically used in organic chemistry.

The term "alkyl" refers to and includes normal and branched chain alkyl groups as well as cycloalkyl groups. The term "lower alkyl", unless specifically stated otherwise, includes normal alkyl of 1 to 6 carbons, branched-chain alkyl of 3 to 6 carbons and cyclo-groups having 3 to 6 carbon atoms. Similarly, the terms "alkenyl" and "alynyl" include normal and branched chain as well as cyclo-alkenyl and alkynyl groups, respectively, having 2 to 6 carbons when the chains are normal, and 3 to 6 carbons when the chains are branched or cyclic.

The terms endo and exo are used in describing a substituent in spatial relation to its connection to a bridged ring and refer to the position of the substituent as either "inside" or "outside" the ring. For the bicycloheptane compounds, endo refers to a substituent attached to the ring by a bond that points down and below the general plane of the six membered ring, and exo refers to a substituent attached to the ring by a bond that points out from and above the general plane of the six membered ring.

The terms cis and trans are also used in describing the relative stereochemistry of the substituents of the present invention. Since the carbon atoms at positions 2 and 3 in the norbornane and biyclo[2.2.2]octane rings are rigidly fixed by the bicyclic ring structure there is no bond rotation or alternative conformation of the ring system. Thus, the bond between carbon atoms 2 and 3 can be likened to a double bond in that respect, and so relative stereochemistry can be described with cis indicating that the substituents are located on the same side of the bond, and trans indicating that the substituents are located in positions opposite one another across the bond.

Pharmaceutically acceptable salts of the compounds of formula I are also within the scope of the present invention. Pharmaceutically acceptable acid addition salts of the compounds of the invention are those formed from acids which provide pharmaceutically acceptable anions, such as the hydrochloride, hydrobromide, hydroiodide, sulfate, bisulfate, phosphate or acid phosphate, acetate, maleate, fumarate, oxalate, lactate, tartrate, citrate, gluconate, saccharate, or p-toluenesulfonate salts. A pharmaceutically acceptable salt may be any salt which retains the activity of the parent compound and does not impart any deleterious or untoward effect on the subject to which it is administered and by the context in which it is administered.

Organic amine salts may be made with amines, particularly ammonium salts such as mono-, di- and trialkyl amines or ethanol amines. Salts may also be formed with caffeine, tromethamine, and similar molecules. Where there is a nitrogen sufficiently basic as to be capable of forming acid addition salts such may be formed with any inorganic or organic acids or alkylating agent such as methyl iodide. Any of a number of simple organic acids such as mono-, di-, or tri-acid may also be used. A pharmaceutically acceptable salt may be prepared for any compound of the invention having a functionality capable of forming such a salt, e.g., an acid salt of an amine functionality.

Utility and Dosage Forms

The compounds of formula I and pharmaceutically acceptable acid addition salts thereof have been found to possess valuable pharmacologic properties in the central nervous system and, in particular, have been shown to block (antagonize) $\alpha_2$ receptors in standard laboratory tests. Accordingly, these compounds and pharmaceutically acceptable compositions containing them are useful in reduction or maintenance of the intraocular pressure in at least one eye of a mammal and in regulation of other physiologic phenomena related to $\alpha_2$ receptors. Such physiologic activities include for example: alleviation, prevention or inhibition of depression in mammals; reduction in the severity of diabetes; alleviation of male impotence; and stimulation of weight loss.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as described below.

Drops and solutions applied directly to the eye are typically sterilized aqueous solutions containing 0.001% to 10%, most preferably 0.005% to 1% of the active ingredient, along with suitable buffer, stabilizer, and preservative. The total concentration of solutes should be such that, if possible, the resultant solution is isotonic with the lachrymal fluid and has a pH in the range of 6–8. Typical sterilizing agents are thimerosal, chlorobutanol, phenyl mercuric nitrate and benzalkonium chloride. Typical buffers are, for example, citrate, phosphate, borate or tromethamine; suitable stabilizers include glycerin and polysorbate 80. The aqueous solutions are formulated by simply dissolving the solutes in a suitable quantity of water, adjusting the pH with suitable acid or base to a pH of about 6.8 to 8, making a final volume adjustment with additional water and sterilizing the resultant solution.

The dosage level of the resulting composition will, of course, depend on the concentration of the drops, the condition of the subject and the individual magnitude of response to treatment. However, a typical ocular composition could be administered at the rate of about 2 to 10 drops per day per eye of a 0.1% solution of active ingredient.

The compounds of the present invention, when administered for conditions which are regulated by the central nervous system (CNS), can be by any of the accepted modes of administration for agents which relieve depression or affect the CNS including oral, parenteral, rectal, and otherwise systemic routes of administration. Any pharmaceutically acceptable mode of administration can be used, including solid, semi-solid, or liquid dosage forms, such as for example, tablets, suppositories, pills, capsules, powders, liquids suspensions, or the like, preferably in unit dosage form suitable to single administration of precise dosages, or in sustained or controlled release forms for the prolonged administration of the compound at a predetermined rate. The compositions will typically include a conventional pharmaceutical carrier or excipient and an active compound of formula I or the pharmaceutically acceptable salts thereof and, in addition, may include other medicinal agents, pharmaceutical agents, carriers, adjuvants, etc.

The amount of active compound administered will of course be dependent of the subject being treated, the severity on the affliction, the manner of administration and the judgment of the prescribing physician. However, an effective dosage is in the range of 0.01–1 mg/kg/day, preferably 0.1–0.5 mg/kg/day. For an average human of about 70 kg, this would amount to 0.7–70 mg/day.

For solid compositions, conventional non-toxic carriers include, for example mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol as a carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol ethanol, and the like to thereby form a solution or suspension. If desired, the pharmaceutical composition to be administered may also contain minor amounts of non toxic auxiliary pH buffering agents and the like, for example, sodium acetate, sorbitan monolaurate, triethanolamine oleate, etc. Actual methods of preparing such dosage forms are known, or will be apparent to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or composition containing active ingredient of formula I or it salts in the range of 0.25 to 95% with the balance made up from non-toxic carrier may be prepared.

For oral administration, a pharmaceutically acceptable non-toxic composition is formed by the incorporation of any of the normally employed excipients, and may contain 1%–95% active ingredient, preferably 5%–50%.

Parenteral administration is generally characterized by injection, whether subcutaneously, intramuscularly, or intravenously. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, triethanolamine oleate, etc.

The percentage of active compound contained in such parenteral compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

Preferred Embodiments

Among the family of compounds of the present invention, a preferred group includes compounds of formula I wherein X is oxygen, i.e. compounds where the oxazoline ring constitutes the heterocycle.

A second preferred group of compounds of the invention are those that incorporate the bicyclo[2.2.1]heptane group in their structure as the ring A group.

Within either of the two preceding preferred groups, a still more preferred embodiment is of compounds which have a hydrogen atom or an aromatic group at the position represented by R.

Methods of Preparation

As illustrated by Scheme I below, treatment of an alkynyl acid with diazomethane in ether afforded the corresponding ester. The ester and cyclopentadiene were warmed at 175° C. for 40 hours to form the cycloadduct. This adduct was unstable to $SiO_2$ chromatography and was best purified using a Kugelrohr distillation.

SCHEME I

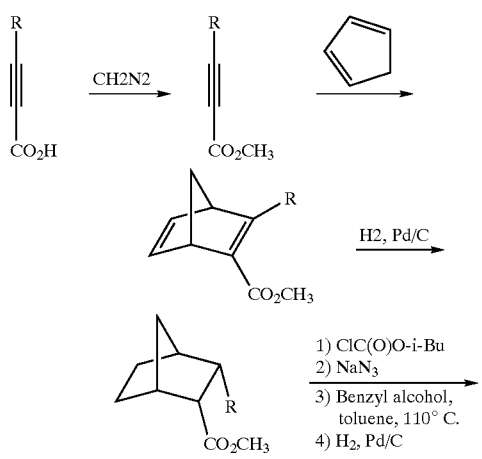

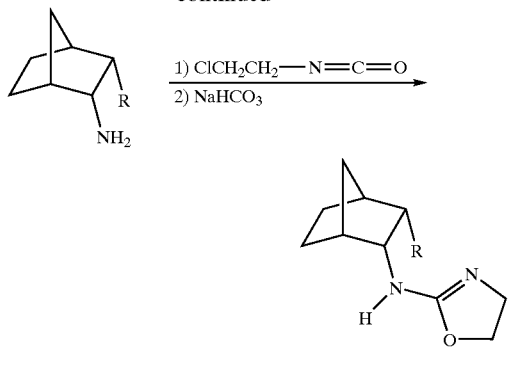

The double bonds in the cycloadduct were immediately saturated by treatment with $H_2$ and Pd/C at one atmosphere. Conversion of the ester into an amine was accomplished by conversion to the carboxylic acid followed by a Curtius reaction. Thus, the add was activated by treatment with isobutylchloroformate. The acyl azide was formed by treatment with sodium azide. Elimination of nitrogen and formation of a benzyl carbamate occurred when the azide was warmed in toluene in the presence of benzyl alcohol. The amine was liberated upon treatment with $H_2$ and Pd/C at one atmosphere. Oxazoline synthesis was accomplished under standard conditions: treatment first with chloroethylisocyanate and then aqueous $NaHCO_3$ solution.

endo, exo Relative Stereochemistry

Preparation of b-nitrostyrene was accomplished according to the Organic Syntheses method. Treatment of a methanol solution of benzaldehyde with nitromethane (100 mol.-%) in the presence of sodium hydroxide (105 mol.-%) afforded the nitro alcohol. Dehydration of the alcohol was effected by treatment with aqueous hydrochloric acid (5M).

The nitrostyrene of 3,4-dihydroxybenzaldehyde was obtained by treating piperonal (3,4-methylenedioxybenzaldehyde) in a similar fashion to that reported for b-nitrostyrene. The acetal proved stable to the aqueous acid required for dehydration.

Construction of the bicyclo[2.2.1]heptane skeleton was carried out in two steps. The Diels-Alder reaction was conducted by warming the nitrostyrene with cyclopentadiene (110 mol.-%) neat (b-nitrostyrene is a low melting material) or in 1,2-dichloroethane (1M in nitroolefin). The Diels-Alder reaction proceeds in approximately a 3:1 endo nitro: exo nitro ratio. Both the ratio and relative stereochemistry was demonstrated through X-ray analysis. Reduction of both the nitro group and the olefin was carried under an atmosphere of hydrogen in the presence of 10 weight-% palladium on charcoal (10%). Separation of isomers was conveniently carried out at this stage using flash chromatography.

Oxazoline synthesis was conducted under standard conditions. The amine was first converted to the chloroethylurea by treatment with chloroethylisocyanate. Warming the chloroethylurea in the presence of sodium bicarbonate afforded the oxazolines. This effort is summarized in Scheme II. Thiazolines and imidazolines were also prepared under standard conditions. Treatment of amines with chloroethylisothiocyanate affords thiazolines directly while treatment with imidazoline-2-sulfonic acid affords the corresponding imidazolines in a single step.

Scheme II

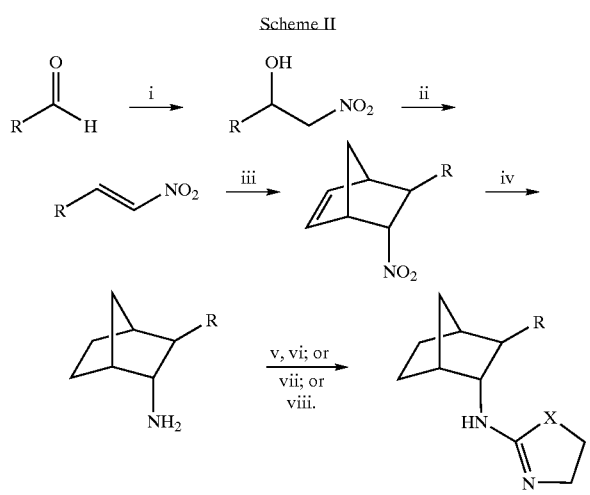

Reagents and Conditions: i. $CH_3NO_2$, KOH, MeOH; ii. HCl; iii. cyclopentadiene, neat or 1M in dichloroethane; iv. $H_2$, 10 Pd on C; v. chloroethylisocyanate; vi. $NaHCO_3$ [X=O]; vii. chloroethylisothio-cyanate [X=S]; viii. imidazoline-2-sulfonic acid [X=NH].

Synthesis of oxabicyclo[2.2.1]heptane derivatives of the present invention can also be prepared by Diels Alder reactions following means well known in the art. Grieco, Zelle, Lis and Finn in *Journal of the American Chemical Society*, 105, 1403–4 (1985) report means of making suitably derivatized oxabicyclo[2.2.1]heptane and oxabicyclo [2.2.1]heptene compounds which can be elaborated into compounds of the present invention. This can be accomplished by the synthetic steps which follow the Diels Alder cyclo addition in Scheme 1 using the 2-carbomethoxy-bicyclo[2.2.1]hept-2-ene intermediate of the reference, or if the nitro functionality of other of the Grieco et al. compounds are employed according to the steps iv, v, vi (or vii or viii) in Scheme 2. Another journal article by Jarvest and Readshaw disclose advantageous conditions for Diels-Alder cyclization of derivatized furans and cyanoacrylate to yield 2-cyano-5-substituted-bicyclo[2.2.1]heptanes. These articles are incorporated by reference herein in their entirety.

The invention is further illustrated by the following non-limiting examples which are illustrative of a specific mode of practicing the invention and are not intended as limiting the scope of the appended claims.

EXAMPLE 1

2-Hydroxy-1-nitrohexane

Pentanal (49.6 ml, 464 mmol) was stirred in a solution of nitromethane (276 ml, 5108 mmol). To the reaction methanolic KOH (3N) was added dropwise to pH 8. The reaction was stirred at room temperature overnight. The solution contained trace amounts of insoluble dark brown mater. The solution was washed with $H_2O$ and extracted into dichloromethane; concentration of the solvent gave clean product (II) in 96% yield, (56.58 g).

EXAMPLE 2

1-Nitrohex-1-ene

The nitroalcohol (1) (2.0 g, 13.6 mmol) was dissolved in dichloromethane and treated at 0° C. for 30 minutes by dropwise addition with methanesulfonyl chloride (1.6 g, 13.6 mmol). Triethylamine (2.75 g, 27.2 mmol) was then added dropwise and stirred for an additional hour at 0° C. The product was washed with 1M $H_3PO_4$ and then with saturated $NaHCO_3$ and extracted with dichloromethane. Concentration of the solvent gave the olefin in 80% yield (3.03 g).

EXAMPLE 3

Trans-2-nitro-3-butyl bicyclo[2.2.1]heptane

The nitroolefin (2) (3.00 g, 19.3 mmol) was dissolved in 20 ml of dichloromethane and then freshly cracked cyclopentadiene (6.49, 96.6 mmol) was added and bubbled with argon for 15 minutes. This was added to a sealable tube and once sealed was placed in an oil bath at 90° C. overnight. The reaction went to completion. Excess cyclopentadiene was removed by Kugelrohr distillation. The resultant product was obtained in 60% yield (3.53 g).

EXAMPLE 4

Trans 2-(3-butyl-bicyclo[2.2.1]heptyl)amine

The cycloadduct (3) (2.53 g, 13.0 mmol) was dissolved in methanol (25 ml) and bubbled with Ar. To this was added 10% palladium on carbon (500 mg). This vessel containing this mixture was put on a Parr apparatus for hydrogenation at 50 psi overnight. The reduced material was filtered through celite and the solvent was concentrated. The residue was dissolved in 1M $H_3PO_4$ and washed with dichloromethane. The aqueous layer was basified with 25% NaOH to a pH of ca. 13. This was extracted with dichloromethane three times. The organic layers were combined and concentrated to give the product in 86% yield (1.86 g).

EXAMPLE 5A

Trans 2-(3-butyl bicyclo[2.2.1]heptyl)amino-oxazoline

The amine (4) (200 mg, 1.20 mmol) was dissolved in THF (5 ml). To this was added chloroethylisocyanate (0.122 ml, 1.40 mmol) dropwise and stirred at room temperature for two hours. The reaction mixture was poured into 1M $H_3PO_4$ and ice (1:1) to quench the reaction. This was then extracted with dichloromethane and concentrated to give the urea. The urea was treated with methanol (6 ml), water (6 ml) and $NaHCO_3$ (202 mg, 2.4 mmol). This mixture was refluxed at 80° C. for 2 hours. The reaction was quenched with saturated $NaHCO_3$ and extracted with dichloromethane. The organic layers were combined and concentrated to give desired product (270 mg). Column chromatography with 5% MeOH saturated with $NH_3$ in dichloromethane gave the desired product in 60% yield (155 mg).

$^1$H NMR($CDCl_3$): 0.70–1.70(M,16H), 1.9(d, 1H), 2.5(5, 1H), 3.4(S1H) 3.75(t,2H)4.1(5,1H), 4.25(t,2H).

| Elemental analysis: | theoretical | C 71.14% | H 10.23% | N 11.86% |
|---|---|---|---|---|
| | found | C 70.8% | H 10.20% | N 11.60% |

5B.

Trans 2-(3-butyl-bicyclo[2.2.1]heptyl) aminothiazoline

The amine (4) (200 mg, 1.20 mmol) in THF (5 ml) was treated with chloroethylisothiocyanate dropwise at 0° C. for 3 hours. The reaction mixture was poured into 1M $H_3PO_4$. The aqueous layer was extracted with dichloromethane and then basified with 25% NaOH to pH 13. The aqueous layer was then extracted with dichloromethane three times. The organic layers were combined and concentrated to give the product in 11.6% yield (35 mg).

$^1$H NMR (CDCl$_3$): 0.85 (t, 3H), 1.1–1.7(M, 13H), 1.95 (d,1H), 2.5 (S, 1H) 3.3 (t,2H), 3.5 (S,1H), 4.0 (t, 2H), $^{13}$C NMR C (CD$_3$OD): d 14.0, 21.0, 23.0, 30.0, 30.5, 35.0, 35.2, 35.3, 40.5, 41.5, 51.5, 64.0.

| Elemental analysis: | theoretical | C 66.63% | H 9.59% | N 11.10% |
|---|---|---|---|---|
| | found | C 66.40% | H 9.52% | N 11.0% |

5C.

Trans 2-(3-butyl-bicyclo[2.2.1]heptyl) aminoimidazoline

An acetonitrile (2.4 ml) suspension of the amine (4) (200 mg, 1.20 mmol) with triethylamine (0.184 ml, 1.32 mmol) and then with imidazoline-2-sulfonic acid (198 mg, 1.32 mmol). The solution was refluxed for 2 hours. Aqueous workup with 1 M $H_3PO_4$ and then basifying aqueous layer to pH 13 and extraction with dichloromethane gave the desired product. The HCl salt was prepared from HCl/ether in methanol which gave a yield of 20% (60 mg).

$^1$H NMR (CDCl$_3$): 0.70–1.70 (M, 16H), 2.0 (d, 1H), 2.6 (S,1H), 3.4(S,1H) 3.65(S,4H)

$^{13}$C NMR (CHCl$_3$): d 22.9, 27.8, 27.89, 28.05, 31.83, 32.29, 33.41, 37.34, 39.89, 42.53, 42.89, 44.06, 44.54, 57.9, 61.6, 95.6, 161.02.

EXAMPLE 6A exo-[2.2.1] bicycloheptyl-2-amino-oxazoline

A THF solution containing the exo-norbornylamine was cooled to 0° C. under a nitrogen atmosphere and was treated with chloroethylisocyanate. The magnetically mixed solution was allowed to warm to r.t. over 1 h and then stirred an additional 1 h at r.t. After extraction from 1 M $H_3PO_4$ (20 mL; 3×15 mL CH$_2$Cl$_2$ extraction) and drying over Na$_2$SO$_4$, the white solid recovered after concentration was warmed at reflux in aqueous MeOH containing NaHCO$_3$. After extraction from 0.5N NaOH, drying (Na$_2$SO$_4$) concentration and chromatography (eluent: 5% NH$_3$-saturated MeOH in CH$_2$Cl$_2$; 230–400 mesh SiO$_2$; eluate collected in 10 mL fractions). Fractions 10–20 afforded 350 mg of the agent (65%). Recrystallization was accomplished using pure hexane.

mp 115–117° C.

$^1$H-NMR (CDCl$_3$): 0.87 (t over m, 5H), 1.1–1.85 (m, 5H), 2.4 (s,1H), 3.78 (t, 2H), 3.85 (s, 1H), 4.25 (t, 2H).

EXAMPLE 6B endo-[2.2.1] bicycloheptyl-2-amino-oxazoline

The amine from Aldrich (as H Cl salt was dissolved in 25% NaOH and extracted 3 times with CH$_2$Cl$_2$, dried over Na$_2$SO$_4$ and concentrated to a waxy foam, dried under vacuum, and treated with choloethylisocyanate as with the exo amine above in 6A.

mp 122–124° C.

$^1$H-NMR (CDCl$_3$): 1.08–1.26 (m, 5H), 1.32–1.85 (m, 5H), 2.28 (br. d,1H), 3.45 (s, 1H), 3.79 (t, 2H), 4.24 (t, 2H).

EXAMPLE 7

2-Carbomethoxy-3-ethyl [2.2.1] bicyclo $\Delta^{2,3}$, $\Delta^{5,6}$ heptadiene Methyl pent-2-ynoate (5.3 g, 126.16 mmol) was dissolved in toluene (30 ml) and placed in a sealable tube. To this was added freshly cracked cyclopentadiene. The tube was sealed and placed in a oil bath at 168° C. for 42 hours. The excess cyclopentadiene was removed by Kugelrohr distillation. The product was isolated in 70.3% yield (526 g).

EXAMPLE 8

Cis 2-carbomethoxy-3-ethyl[2.2.1]bicycloheptane

The cycloadduct (6) (5.26 g, 29.5 mmol) was dissolved in MeOH (60 ml), and bubbled with Ar, and to the solution was added 10% palladium on carbon (500 mg). The reaction vessel containing this mixture was put on a Parr apparatus for hydrogenation at 50 psi overnight. The reduced material was filtered through celite and solvent concentrated. The residue was dissolved in 1M $H_3PO_4$ and washed with dichloromethane. The aqueous layer was basified with 25% NaOH to ca. pH 13. This was extracted with dichloromethane three times. The organic layers were combined and concentrated to give product in 81% yield (4.7 g).

EXAMPLE 9

Cis 2(3-ethyl-biyclo[2.2.1]heptyl) amine

The ester (3) (2.0 g, 10.2 mmol) was dissolved in a MeOH/THF (30 ml/20 ml) solution. This was treated with 2N LiOH (10.2 ml, 20.4 mmol) in H$_2$O at 100° C. and refluxed. The reaction was concentrated to a paste and dissolved in 40 ml H$_2$O and washed twice with dichloromethane. The organic layers were combined and concentrated to give the corresponding acid. This acid was dissolved in acetone (20 ml), and triethylamine (3.06 ml, 22.1 mmol) was added dropwise. Next ethylchloroformate was added dropwise (2 ml, 20.9 mmol) at 0° C. The reaction was stirred for 1 hour. NaN$_3$ (676 mg, 10.4 mmol) was added in portions at 0° C. for an additional hour. The reaction was partitioned between ice water and dichloromethane. The organic layers were combined and concentrated to give the acyl azide. This was then treated with benzyl alcohol (995 mg, 9.2 mmol) in toluene and refluxed at 110° C. for 30 minutes. The reaction was washed with H$_2$O and extracted in dichloromethane. Concentration of solvent gave the benzyl carbamate. The carbamate was reduced in the same manner as before with 10% palladium on carbon. The product was obtained in an overall yield of 45% (550 mg).

NMR H$^1$(CDCl$_3$): 0.8(t, 3H), 1.0–1.6(m, 9H), 1.8 (s,1H), 2.2 (s,1H), 4.7(s,1H), 5.3(s,2H)

EXAMPLE 10A

Cis 2-(3-ethyl-bicyclo[2.2.1]heptyl) amino-oxazoline

The bicyclic amine (8) was treated as in the procedure outlined for the preparation of the trans compound (5A) above.

$^1$H-NMR (CDCl$_3$): 0.8(t, 3H), 1.00–2.00(m, 9H), 2.1(s, 1H), 2.5(s,1H), 3.9(s,1H), 3.8(t, 2H), 4.2(t, 2H).

$^{13}$C NMR (CDCl3): d 14.5, 20.8, 25.5, 28.2, 38.2, 40.3, 44.7, 54.42, 55.05, 64.3, 69.2.

| | |
|---|---|
| Analysis calculated for $C_{12}H_{20}N_2O$: | C 69.09, H 9.68, N 13.45 |
| Found: | C 68.6, H 9.24, N 13.45. |

EXAMPLE 10B

Cis 2-(3-ethyl bicyclo[2.2.1]heptyl) aminothiazoline can be prepared by substituting the bicyclic amine (8) for (4) in the preparation of 5B above.

EXAMPLE 10C

Cis 2-(3-ethyl-bicyclo[2.2.1]heptyl) aminoimidazoline

Likewise, 9C can be prepared by substituting the bicyclic amine (8) for (4) in the preparation of 5C above.

EXAMPLE 11

2-N-Bornylamino-oxazoline

To a THF solution of the amine (250 mg, 1.63 mmol) at 0° C. was added chloroethylisocyanate (189 mg, 1.79 mmol) dropwise. The reaction was allowed to warm to r.t. and after stirring for one hr., all starting material was consumed. The reaction mixture was poured into 1M $H_3PO_4$ and extracted three times with methylene chloride. After drying, the solution was concentrated and the resulting solid was warmed in aqueous methanolic $NaHCO_3$. The reaction was extracted from 0.5N NaOH and dried ($Na_2SO_4$), concentrated and chromatographed over 250–400 mesh silica using 5% ammonia saturated methanol in $CH_2Cl_2$ as eluent. Yield: 206 mg (60%).

$^{13}$C NMR (CDCl3) 161.7, 67.6, 57.8, 52.9, 49.2, 48.0, 44.8, 38.4, 28.3, 27.6, 19.9, 18.7, 13.7

$^1$H NMR (CDCl$_3$) 4.24 (2H, m); 3.80 (3H, m); 2.38 (1H, m); 1.87–1.1 (6H, env, m); 0.93 (3H, s); 0.87 (3H, s); 0.86 (3H, s)

EXAMPLE 12

Bicyclo[2.2.2]octane aminooxazoline
Adamantylaminooxazoline

In a similar manner to Example 10, commercially available bicyclo[2.2.2]octane amine and adamantylamine can be used to prepare the 2-bicyclo[2.2.2]octane-aminooxazoline and adamantylaminooxazoline compounds, respectively.

EXAMPLE 13

Receptor Binding Assays

13A.

Tissue preparation: Membrane suspensions were prepared from human cerebral cortex (HCC) obtained from the UCI Organ and Tissue Bank and rat kidney cortex (RKC). Briefly, tissues (1 g) were homogenized in 25 ml of iced-cold 5 mM tris, pH 7.4 with a Polytron homogenizer for 30 secs at setting# 7, and centrifuged for. 10–12 minutes at 300×g at 4° C. The supernatant was filtered: through 2 layers of gauze and diluted 1:2 with 50 mM Tris-HCI buffer, pH 7.4, then centrifuged at 49,000×g for 20 minutes. The pellet fraction was washed 3 times (resuspended in Tris-HCl buffer and centrifuged for 20 minutes at 49,000×g). The pellet was then stored at −80° C. until the binding assay.

Cell preparation: HT-29 and chinese hamster ovary (CHO) cells expressing the human $\alpha_{2A}$ (CHO—C10) receptor and CHO cells (CHO—RNG) expressing the rat $\alpha_{2B}$ adrenoceptor were grown to near confluency in Dulbecco's modified Eagle's medium supplemented with 10% fetal bovine serum using standard cell culture methods. Cells were harvested by scraping and placed into cold buffer of the following composition: 50 mM Tris-HCl, 5 mM EDTA, pH 7.4). Cells were then homogenized with a Polytron homogenizer for 2×10 secs at setting # 7, arid centrifuged for 20 minutes at 49,000×g. The pellet fraction was washed (resuspended in Tris-HCl, pH 8 buffer and centrifuged for 15–20 minutes at 49,000×g) 2 times and stored at −100° C. until binding assay.

Binding studies: The radioligands [$^3$H]rauwolscine (specific activity 80 Ci/mmol) and [$^3$H]prazosin (specific activity 76 Ci/mmol) were obtained from New England Nuclear, Boston, Mass. Frozen membrane pellet was resuspended in 25 mM glycine/glycine, pH 7.4 and incubated with radioligand under the following conditions: CHO—C10, CHO—RNG, HT-29-[$^3$H]rauwolscine, 22° C., 30 minutes; RKC-[$^3$H]rauwolscine, 0° C., 120 minutes; and, HCC-[$^3$H]prazosin, 22° C., 30 minutes in a final volume of 500 μl. At the end of the incubation period, the samples were filtered through glass fiber filters (Whatman GF/B) in a 96 well cell harvester and rapidly washed four times with 4 ml of ice-cold 50 mM, Tris-HCl buffer. The filters were then oven dried and transferred to scintillation vials containing 5 ml of Beckman's Ready Protein® scintillation cocktail for counting. Specific binding defined by 10 μM phentolamine for competition studies were as follows: 0.3 nM [$^3$H] rauwolscine—CHO—C10 99%; 0.4 nM[$^3$H]rauwolscine —CHO—RNG 99%; 0.7;nM [$^3$H]rauwolscine—HT-29 90%; 1 nm [$^3$]rauwolscine—RKC 92%, and 0.3 nM [$^3$H] prazosin—HCC 87%. Protein concentrations were determined with a protein assay kit from Bio Rad. Binding isotherms, equilibrium dissociation and affinity constants were analyzed and determined by the non-linear least squares curve fitting programs AccuFit Competition/ Saturation by Beckman.

Binding studies: The radioligands [$^3$H]rauwolscine (specific activity 80 Ci/mmol), [$^3$H]prazosin (specific activity 76 Ci/mmol) and [$^3$H]brimonidine (UK-14,304; specific activity 63 Ci/mmol) were obtained from New England Nuclear, Boston, Mass. Frozen membrane pellet was resuspended either 50 mM tris, 2 mM EGTA, 1 mM $MgCl_2$, pH7.5 (RbKC, RbICB-[$^3$H]brimonidine); 50 mM tris, 0.5 mM EDTA, 5 mM NaCl, pH 7.7 (RbICB-[$^3$H]rauwolscine); 25 mM glycine/glycine, pH 7.4 (RtKC, CHO—C10, CH—RNG, HT-29, HCC) or 50 mM tris, 0.1 mM $MnCl_2$, pH7.7 (RtCC). Membrane protein homogenate (75–200 μg) was incubated with radioligand under the following conditions: RbKC and RbICB-[$^3$H]rauwolscine, 22° C., 45 minutes; RtCC and RbICB-[$^3$H]brimondine, 22° C., 90 minutes; CHO—C10, CHO—RNG and HT-29-[$^3$H]rauwolscine, 22° C., 30 minutes; HCC—[$^3$H]prazosin, 22° C., 30 minutes; and, in a final volume of 250 or 500 μl. At the end of the incubation period, the samples were filtered through glass fiber filters (Whatman GF/B) in a 24 or 96 well cell harvester and rapidly washed four times with 4 mls of iced-cold 50 mM Tris-HCl buffer. The filters were then oven dried and transferred to scintillation vials containing 10 mls of, Beckman's Ready Protein® scintillation cocktail for counting. Specific binding defined by 10 μM phentolamine for competition studies were as follows: 2.4 nM [$^3$H]brimonidine-RbICB 62%; 2.4 nM [$^3$H]rauwolscine-RbICB 75%; 2 nM [$^3$H]rauwolscine-RbKC 88%; 0.3 nM [$^3$H]rauwolscine- CHO—C10 99%; 0.4 nM [³H]rauwolscine-CHO—RNG 99%, 0.3 nM [³H]prazosin 87%; and 1 nM [³H]rauwolscine-RtCC 90%. Protein concentrations were determined with a protein assay kit from Bio Rad. Binding isotherms, equilibrium dissociation and affinity constants were analyzed and determined by the non-linear least squares curve fitting programs EBDA (BioSoft) or AccuFit Competition/Saturation by Beckman.

13B.

Cell preparation: Chinese hamster ovary (CHO) cells expressing the human $\alpha_{2A}$ (CHO—C10) and the rat $\alpha_{2B}$ (CHO—RNG) adrenoceptors were grown to near confluency in Dulbecco's modified Eagle's medium supplemented with 10% fetal bovine serum using standard cell culture methods. Cells were harvested by scraping and placed into cold buffer of the following composition: 50 mM Tris-HCl, 5 mM EDTA, pH 7.4). Cells were then homogenized with a Polytron homogenizer for 2×10 secs at setting #7, and centrifuged for 20 minutes at 49,000×g. The pellet fraction was washed (resuspended in Tris-HCl, pH 8 buffer and centrifuged for 15–20 minutes at 49,000×g) 2 times and stored at −100° C. until binding assay.

13C.

Binding Studies: Determination of $K_i$

The radioligands [³H]rauwolscine (specific activity 80 Ci/mmol) and [³H]prazosin (specific activity 76 Ci/mmol) were obtained from New England Nuclear, Boston, Mass. Frozen membrane pellet was resuspended in 25 mM glycine/glycine, pH 7.4 and incubated with radioligand under the following conditions: CHO—C10, CHO—RNG-[³H]rauwolscine, 22° C., 30 minutes; and, HCC—[³H]prazosin, 22° C., 30 minutes in a final volume of 500 ul. At the end of the incubation period, the samples were filtered through glass fiber filters (Whatman GF/B) in a 96 well cell harvester and rapidly washed four times with 4 mls of iced-cold 50 mM Tris-HCl buffer. The filters were then oven dried and transferred to scintillation vials containing 5 ml of Beckman's Ready Protein® scintillation cocktail for counting. Specific binding defined by 10 μM phentolamine for competition studies were as follows: 0.3 nM [³H]rauwolscine-CHO—C10 99%; 0.4 nM [³H]rauwolscine-CHO—RNG 99%, and 0.3 nM [³H]prazosin—HCC 87%. Protein concentrations were determined with a protein assay kit from Bio Rad. Binding isotherms, equilibrium dissociation and affinity constants were analyzed and determined by the non-linear least squares curve fitting programs AccuFit Competition/Saturation by Beckman.

Determination of $\alpha_2$ Activation: Measuring Efficacy ($EC_{50}$)

Vas Deferens: The prostatic ends of the vas deferens (2–3 cm) were removed from albino rabbits and mounted between platinum electrodes in 9 ml organ baths containing Krebs-Hensleit solution of the following composition (mM): NaCl 119, KCl 4.7 MgSO$_4$ 1.5, KH$_2$PO$_4$ 1.2.CaCl$_2$ 25, NaHCO$_3$ 25 and glucose 11. This solution was maintained at 35° C. and bubbled with 95% O$_2$ and 5% CO$_2$. The tissue a was equilibrated at 0.5 g tension for 30 minutes. The vas deferens strips were then field stimulated at 0.1 Hz, 2 msec, 90 mA using a square wave stimulator (World Precision Instruments A310 Accupulser/A385 Stimulus Isolater), or a Grass S48 stimulator at 0.1 Hz, 20 msec, 70 volts. After 30 minutes of electrical stimulation, cumulative concentration-response curves in 0.25 log units were obtained with a 4 minute contact time for each concentration. Each tissue was used to evaluate only one drug. Tissue contractions produced by the field stimulation were measured isometrically using Grass FT-0.03 force-displacement transducers and recorded on a Grass Model 7D physiograph. The reduction in electrically-evoked peak height by the drugs was measured and expressed as a percentage of the pre-drug peak height. The $IC_{50}$ was determined as the concentration which produced a 50% reduction in peak height.

TABLE I

| Structure tested | $K_i$ (nM) | | | $EC_{50}$ (nM) |
| --- | --- | --- | --- | --- |
| | $\alpha_1$ | $\alpha_{2A}$ (CHO-C10) (HT-29)* | $\alpha_{2B}$ (CHO-RNG)(RKC)[†] | $\alpha_2$ (vas def.) |
| 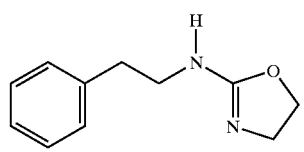 | 11,131 | 1,751 | 4,174 | >56,200 |
| 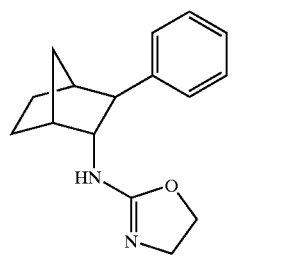 | 1,864 | 3.1 | 7.8 | 29,000 |

TABLE I-continued

| Structure tested | $K_i$ (nM) | | | $EC_{50}$ (nM) $\alpha_2$ (vas def.) |
|---|---|---|---|---|
| | $\alpha_1$ | $\alpha_{2A}$ (CHO-C10) (HT-29)* | $\alpha_{2B}$ (CHO-RNG)(RKC)† | |
| (norbornyl-phenyl-NH-imidazoline) | 6.730 | 14.3 | 72 | >56,200 |
| (norbornyl-phenyl-NH₂) | 10,977 | 6,571 | 6,103 | not tested as no binding was observed |
| (norbornyl-Ph-NH-oxazoline) | 73 | 1.9 | 27 | 3,700 |
| (norbornyl-benzodioxole-NH-oxazoline) | 1,860 | 1.1 | 4.6 | >56,000 |
| (butyl-NH-oxazoline) | >100,000 | 150* | 317† | 1,100 |
| (norbornyl-ethyl-NH-oxazoline) | 24,760 | 59 | 616 | not tested |
| (norbornyl-ethyl-NH₂) | >100,000 | 67,247 | 57,075 | not tested as no binding observed |

TABLE I-continued
| Structure tested | $K_i$ (nM) | | | $EC_{50}$ (nM) |
| --- | --- | --- | --- | --- |
| | $\alpha_1$ | $\alpha_{2A}$ (CHO-C10) (HT-29)* | $\alpha_{2B}$ (CHO-RNG)(RKC)† | $\alpha_2$ (vas def.) |
| 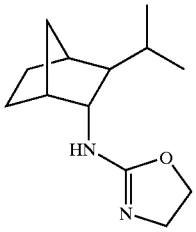 | >10,000 | 43* | 58† | not tested |
| 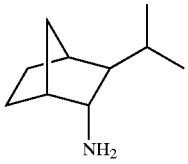 | >100,000 | 23,320 | 20,950 | not tested |
| 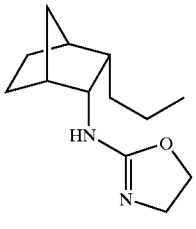 | 8,600 | 25 | 256 | 903 |
| 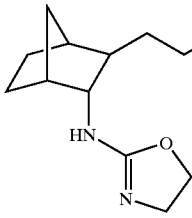 | 8,851 | 9.8 | 28.1 | 46,000 |
| 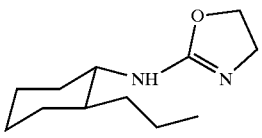 | 1,600 | 0.6 | 8.3 | 1.0 |
| 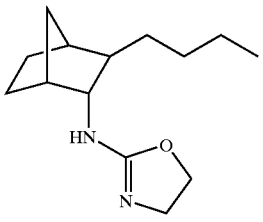 | 5,824 | 29* | 59† | not tested |
| 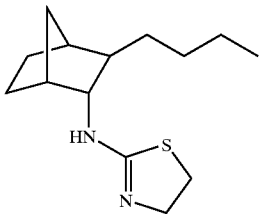 | 42,000 | 58* | 167† | not tested |

TABLE I-continued

| Structure tested | $K_i$ (nM) | | | $EC_{50}$ (nM) $\alpha_2$ (vas def.) |
|---|---|---|---|---|
| | $\alpha_1$ | $\alpha_{2A}$ (CHO-C10) (HT-29)* | $\alpha_{2B}$ (CHO-RNG)(RKC)† | |
| [structure] | 17,240 | 288* | 5,100† | not tested |
| [structure] | >10,000 | 4.2 | 11.5 | >10,000 |
| [structure] | >10,000 | 368 | 1,935 | 16,000 |
| [structure] | 32,487 | 119 | 770 | >10,000 |
| [structure] | >10,000 | 102 | 358 | >5,000 |
| [structure] | 34,950 | 352 | 1,838 | >10,000 |

*HT-29($\alpha_{2A}$)
†Rat Kidney Cortex ($\alpha_{2AB}$)

Several modifications of the above described compounds, the processes disclosed for making them, and application of the disclosed processes to numerous compounds beyond the examples set forth above, may be practiced by those skilled in the art without departing from the scope and spirit of the present invention. Therefore the scope of the present invention should be interpreted solely from the following claims, as such claims are read in light of the present disclosure.

What is claimed is:

1. A method for treating a mammal having a disease state selected from the group consisting of elevated intraocular pressure, depression, non insulin-dependent diabetes, male impotence and obesity which is alleviated by treatment with an $\alpha_2$ blocking agent, which comprises administering a therapeutically effective amount of a compound of the formula I

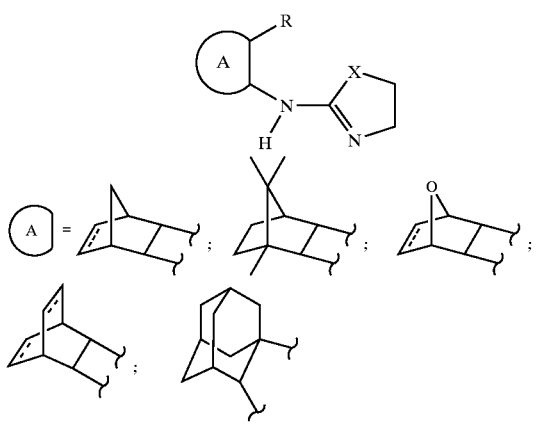

in which: ring A is one of the five alternative multi-cyclic rings as shown wherein a dotted line adjacent to a bond indicates that a single bond or a double bond may be present at that position; X is oxygen or sulfur; R is hydrogen or branched chain alkyl of 1 to 6 carbon atoms, or straight or branched chain alkenyl of 2 to 6 carbon atoms, a cycloaliphatic ring of 3 to 6 carbon atoms, phenyl optionally mono- or di-substituted with hydroxy, halogen, alkyl of 1 to 3 carbon atoms or alkoxy of 1 to 2 carbon atoms, or methylenedioxyphenyl; or a stereoisomer, or a pharmaceutically acceptable salt thereof.

2. The method of claim 1 wherein X is oxygen.

3. The method of claim 1 wherein X is sulfur.

4. The method of claim 1 wherein the ring A is bicyclo [2.2.1]heptane (norbornane).

5. The method of claim 1 wherein R is hydrogen; phenyl optionally mono- or di-substituted with hydroxy, halogen, alkyl of 1 to 3 carbon atoms or alkoxy of 1 to 2 carbon atoms; or is methylenedioxyphenyl.

6. The method of claim 1 wherein said disease state is elevated intraocular pressure.

7. The method of claim 1 wherein said disease state is depression.

8. The method of claim 1 where said disease state is non insulin-dependent diabetes.

9. The method of claim 1 wherein said disease state is male impotence.

10. The method of claim 1 wherein said disease state is obesity.

* * * * *

UNITED STATES PATENT AND TRADEMARK OFFICE
CERTIFICATE OF CORRECTION

PATENT NO. : 6,706,747 B2  
DATED : March 16, 2004  
INVENTOR(S) : Munk et al.

It is certified that error appears in the above-identified patent and that said Letters Patent is hereby corrected as shown below:

Column 9,  
Line 57, delete "mater" and insert in place thereof -- material --

Column 12,  
Line 11, delete "(526 g)" and insert in place thereof -- (5.26 g) --

Column 14,  
Line 34, delete "1 nm" and insert in place thereof -- 1 nM --  
Line 46, before "either" insert -- in --  
Line 47, delete "pH7.5" and insert in place thereof -- pH 7.5 --  
Line 50, delete "CH-RNG" and insert in place thereof -- CHO-RNG --  
Line 51, delete "pH7.7" and insert in place thereof -- pH 7.7 --

Column 16,  
Line 18, delete "25" and insert in place thereof -- 2.5 --  
Line 21, delete "a"

Signed and Sealed this

First Day of June, 2004

JON W. DUDAS  
*Acting Director of the United States Patent and Trademark Office*